US007994354B2

(12) United States Patent
Benecke et al.

(10) Patent No.: US 7,994,354 B2
(45) Date of Patent: Aug. 9, 2011

(54) METHODS FOR PRODUCTION OF POLYOLS FROM OILS AND THEIR USE IN THE PRODUCTION OF POLYESTERS AND POLYURETHANES

(75) Inventors: Herman Paul Benecke, Columbus, OH (US); Daniel B. Garbark, Blacklick, OH (US); Bhima Rao Vijayendran, Kuala Lumpur (MY)

(73) Assignee: Battelle Memorial Institute, Columbus, OH (US)

( * ) Notice: Subject to any disclaimer, the term of this patent is extended or adjusted under 35 U.S.C. 154(b) by 402 days.

(21) Appl. No.: 11/912,546

(22) PCT Filed: Apr. 26, 2006

(86) PCT No.: PCT/US2006/016022

§ 371 (c)(1),
(2), (4) Date: Sep. 26, 2008

(87) PCT Pub. No.: WO2007/027223

PCT Pub. Date: Mar. 8, 2007

(65) Prior Publication Data

US 2009/0216040 A1 Aug. 27, 2009

Related U.S. Application Data

(60) Provisional application No. 60/674,993, filed on Apr. 26, 2005.

(51) Int. Cl.
*C07C 51/34* (2006.01)
*C07C 271/00* (2006.01)
*C11C 3/00* (2006.01)

(52) U.S. Cl. ............ 554/133; 554/169; 554/1; 554/132; 560/157; 560/155; 560/158; 560/129

(58) Field of Classification Search ........................ None
See application file for complete search history.

(56) References Cited

U.S. PATENT DOCUMENTS

| | | | | |
|---|---|---|---|---|
| 3,024,260 | A * | 3/1962 | Ernst | 554/66 |
| 4,055,606 | A | 10/1977 | Prevorsek et al. | |
| 4,242,254 | A | 12/1980 | Abolins | |
| 6,130,297 | A | 10/2000 | Ramesh | |
| 6,974,846 | B2 | 12/2005 | Garrison et al. | |
| 7,122,250 | B2 | 10/2006 | Kinsho et al. | |
| 2004/0108219 | A1 * | 6/2004 | Matsumura et al. | 205/441 |
| 2008/0081883 | A1 | 4/2008 | King, II et al. | |

FOREIGN PATENT DOCUMENTS

DE 1941522 A1 4/1971

(Continued)

OTHER PUBLICATIONS

Office Action pertaining to U.S. Appl. No. 11/864,043 dated Aug. 25, 2010.

(Continued)

*Primary Examiner* — Jafar Parsa
*Assistant Examiner* — Yate K Cutliff
(74) *Attorney, Agent, or Firm* — Dinsmore & Shohl LLP

(57) ABSTRACT

Methods to convert biobased oils, oil derivatives, and modified oils to highly functionalized esters, ester polyols, amides, and amide polyols. The products can be used to make polyurethane and polyester films and foams.

21 Claims, 11 Drawing Sheets

FOREIGN PATENT DOCUMENTS

WO WO 03/050081 A1 * 6/2003
WO 2006/020716 A1 2/2006

OTHER PUBLICATIONS

US Office Action dated Feb. 16, 2010 pertaining to U.S. Appl. No. 11/864,043.

International Search Report and Written Opinion dated Jun. 22, 2010 pertaining to International application No. PCT/US2009/069921.

International Search Report and Written Opinion dated Jun. 10, 2010 pertaining to International application No. PCT/US2009/069932.

Petrovic, Zoran S. "Polyurethanes from Vegetable Oils" Polymer Reviews, vol. 48, No. 1, Jan. 1, 2008, pp. 109-155.

Sparks, Jr. "Oxidation of Lipids in a Supercritical-Fluid Medium" Literature review, reaction of oleic acid with gas oxidants; references "chapter III", Mississippi State University, Mississippi US, May 2008, pp. 33-40, 68.

Partial International Search Report of The International Searching Authority pertaining to International Appln. No. PCT/US2010/000775, dated Aug. 10, 2010.

International Search Report and Written Opinion of the International Searching Authority pertaining to International Appln. No. PCT/US2010/000775, dated Oct. 26, 2010.

EPO Second Examination Report relating to EPO Patent Application No. 06824715.4, dated Feb. 24, 2011.

Extended European search report relating to EPO Application No. 10184843.0, dated Mar. 01, 2011.

* cited by examiner

Notes: $BF_3$ is typically used as catalyst in the reaction of the Aldehyde with $R'OH(OH)_n$ in the upper pathway.

The final product is typically an ester polyol, $RCO_2R'(OH)_n$.

Direct Amidification of Soybean Oil

Transesterification of Soybean Oil

Major Azelaic ($C_9$) Components in Soybean Oil Ester Polyols and Mixed Polyols Azelaic bis(1-Monoglyceride)
Functionality = 4

A

Acetate-Capped Azelaic bis(1-Monoglyceride)
Functionality = 3

B

Azelaic bis(1-Propylene Glycol Ester)
Functionality = 2

C

Hybrid Azelaic 1-Monoglyceride 1-Propylene Glycol Ester
Functionality = 3

D

Azelaic Amide Polyols and Hybrid Amide Polyols

Azelaic Bis(Diethanolamide)
Functionality = 4

A

Azelaic Bis(N-Ethylethanolamide)
Functionality = 2

B

Azelaic Bis(N-Methylethanolamide)
Functionality = 2

C

Azelaic Bis(Ethanolamide)
Functionality = 2

D

Hybrid Azelaic Diethanolamide XXX

E

Hybrid Soybean Ester and Amide polyols

Hybrid Azelaic 1-Monoglyceride Diethanolamide
Functionality = 4

A

Hybrid Azelaic 1-Propylene Glycol Ester Diethanolamide
Functionality = 3

B

Hybrid Azelaic 1-Propylene Glycol N-Methylethanolamide
Functionality = 2

C

METHODS FOR PRODUCTION OF POLYOLS FROM OILS AND THEIR USE IN THE PRODUCTION OF POLYESTERS AND POLYURETHANES

BACKGROUND OF THE INVENTION

The invention provides for methods to convert vegetable and/or animal oils (e.g. soybean oil) to highly functionalized alcohols in essentially quantitative yields by an ozonolysis process. The functionalized alcohols are useful for further reaction to produce polyesters and polyurethanes. The invention provides a process that is able to utilize renewable resources such as oils and fats derived from plants and animals.

Polyols are very useful for the production of polyurethane-based coatings and foams as well as polyester applications. Soybean oil, which is composed primarily of unsaturated fatty acids, is a potential precursor for the production of polyols by adding hydroxyl functionality to its numerous double bonds. It is desirable that this hydroxyl functionality be primary rather than secondary to achieve enhanced polyol reactivity in the preparation of polyurethanes and polyesters from isocyanates and carboxylic acids, anhydrides, acid chlorides or esters, respectively. One disadvantage of soybean oil that needs a viable solution is the fact that about 16 percent of its fatty acids are saturated and thus not readily amenable to hydroxylation.

One type of soybean oil modification described in the literature uses hydroformylation to add hydrogen and formyl groups across its double bonds, followed by reduction of these formyl groups to hydroxymethyl groups. Whereas this approach does produce primary hydroxyl groups, disadvantages include the fact that expensive transition metal catalysts are needed in both steps and only one hydroxyl group is introduced per original double bond. Monohydroxylation of soybean oil by epoxidation followed by hydrogenation or direct double bond hydration (typically accompanied with undesired triglyceride hydrolysis) results in generation of one secondary hydroxyl group per original double bond. The addition of two hydroxyl groups across soybean oil's double bonds (dihydroxylation) either requires transition metal catalysis or stoichiometric use of expensive reagents such as permanganate while generating secondary rather than primary hydroxyl groups.

The literature discloses the low temperature ozonolysis of alkenes with simple alcohols and boron trifluoride catalyst followed by reflux to produce esters. See J. Neumeister, et al., Angew. Chem. Int. Ed., Vol. 17, p. 939, (1978) and J. L. Sebedio, et al., Chemistry and Physics of Lipids, Vol. 35, p. 21 (1984). A probable mechanism for the low temperature ozonolysis discussed above is shown in FIG. 1. They have shown that a molozonide is generated at relatively low temperatures in the presence of an alcohol and a Bronsted or Lewis acid and that the aldehyde can be captured by conversion to its acetal and the carbonyl oxide can be captured by conversion to an alkoxy hydroperoxide. In the presence of ozone the aldehyde acetal is converted to the corresponding hydrotrioxide at relatively low temperatures. If the reaction temperature is then raised to general reflux temperature, the hydrotrioxide fragments to form an ester by loss of oxygen and one equivalent of original alcohol. At elevated temperatures, and in the presence of an acid such as boron trifluoride, the alkoxy hydroperoxide will eliminate water to also form an ester in essentially quantitative yields. This overall process converts each olefinic carbon to the carbonyl carbon of an ester group so that two ester groups are produced from each double bond.

SUMMARY OF THE INVENTION

One broad embodiment of the invention provides for a method for producing an ester. The method includes reacting a biobased oil, oil derivative, or modified oil with ozone and excess alcohol at a temperature between about −80° C. to about 80° C. to produce intermediate products; and refluxing the intermediate products or further reacting at lower than reflux temperature; wherein esters are produced from the intermediate products at double bond sites, and substantially all of the fatty acids are transesterified to esters at the glyceride sites. The esters can be optionally amidified, if desired.

Another broad embodiment of the invention provides a method for producing amides. The method includes amidifying a biobased oil, or oil derivative so that substantially all of the fatty acids are amidified at the glyceride sites; reacting the amidified biobased oil, or oil derivative with ozone and excess alcohol at a temperature between about −80° C. to about 80° C. to produce intermediate products; refluxing the intermediate products or further reacting at lower than reflux temperature, wherein esters are produced from the intermediate products at double bond sites to produce a hybrid ester/amide.

BRIEF DESCRIPTION OF THE INVENTION

DETAILED DESCRIPTION OF THE INVENTION

Broadly, the present invention provides for the ozonolysis and transesterification of biobased oils, oil derivatives, or modified oils to generate highly functionalized esters, ester alcohols, amides, and amide alcohols. By biobased oils, we mean vegetable oils or animal fats having at least one triglyceride backbone, wherein at least one fatty acid has at least one double bond. By biobased oil derivatives, we mean derivatives of biobased oils, such as hydroformylated soybean oil, hydrogenated epoxidized soybean oil, and the like wherein fatty acid derivatization occurs along the fatty acid backbone. By biobased modified oils, we mean biobased oils which have been modified by transesterification of the fatty acids at the triglyceride backbone.

Figure 2:
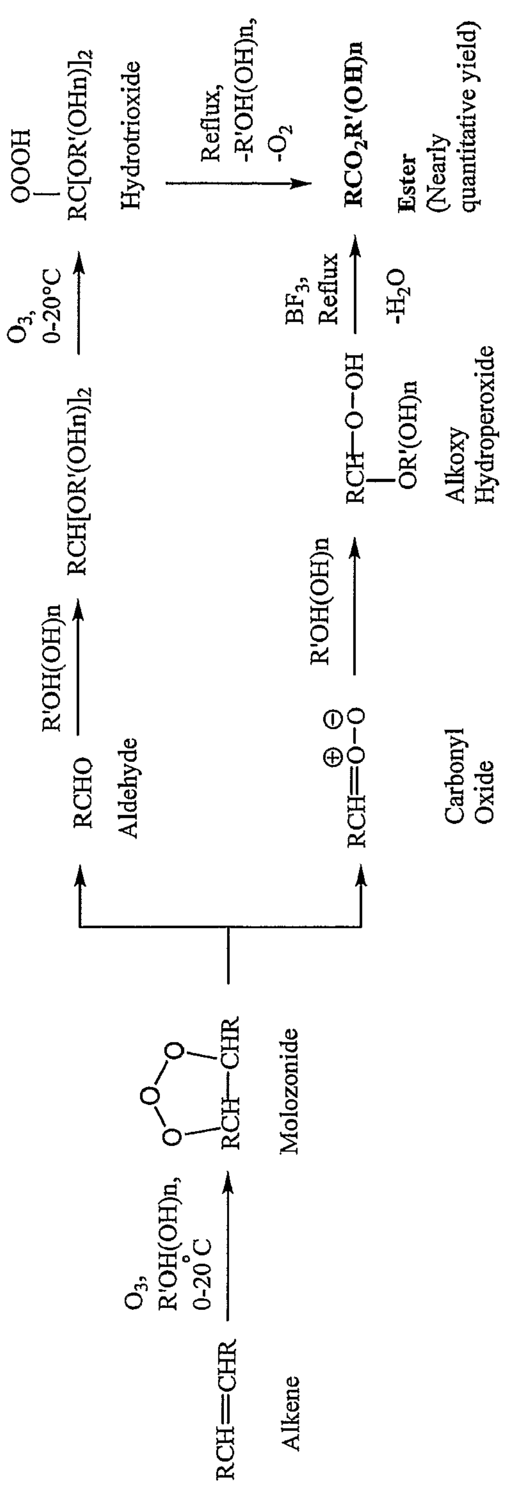
FIG. 2 is a schematic depicting the reactions involved in the two stage ozonolysis of a generalized double bond in the presence of a polyol and the catalyst boron trifluoride.

Ozonolysis of olefins is typically performed at moderate to elevated temperatures whereby the initially formed molozonide rearranges to the ozonide which is then converted to a variety of products. Although not wishing to be bound by theory, it is presently believed that the mechanism of this rearrangement involves dissociation into an aldehyde and an unstable carbonyl oxide which recombine to form the ozonide. The disclosure herein provides for low temperature ozonolysis of fatty acids that produces an ester alcohol product without any ozonide, or substantially no ozonide as shown in FIG. 2. It has been discovered that if a polyol such as glycerin is used in this process (and in excess) that mainly one hydroxyl group will be used to generate ester functionality and the remaining alcohol groups will remain pendant in generating ester glycerides.

Figure 1:
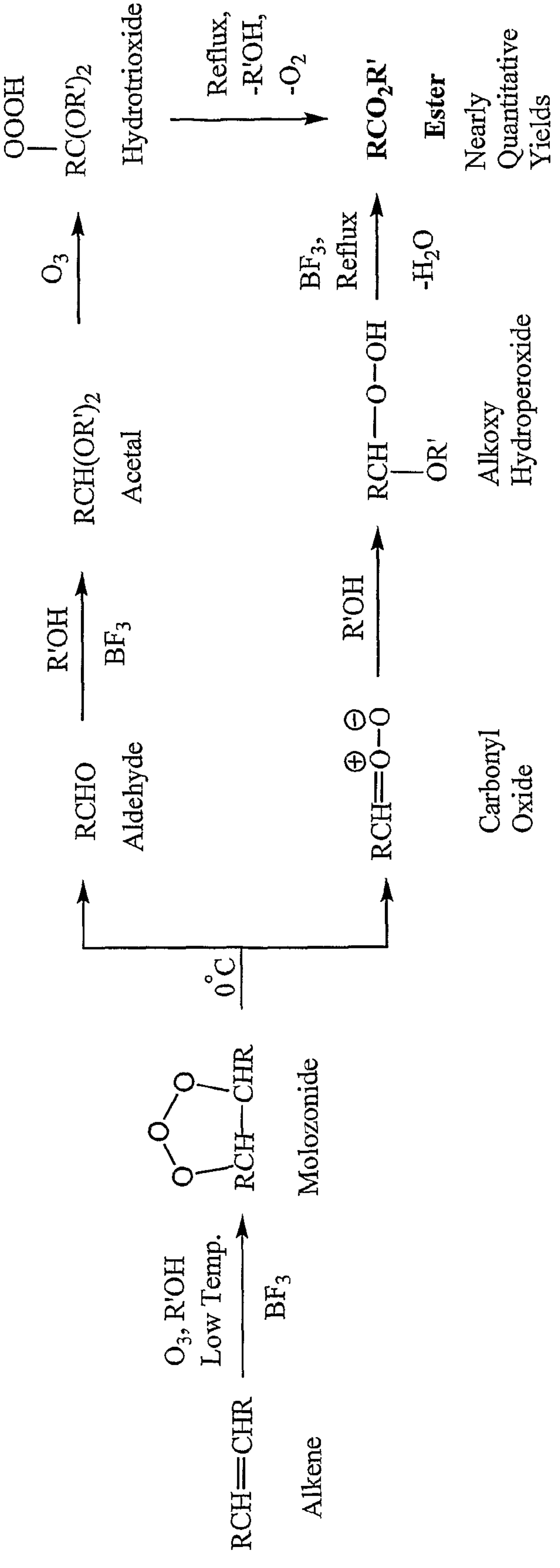
FIG. 1 is a schematic depicting the reactions involved in the two stage ozonolysis of a generalized double bond in the presence of an alcohol and the catalyst boron trifluoride.

One basic method involves the combined ozonolysis and transesterification of a biobased oil, oil derivative, or modified oil to produce esters. As shown in FIG. 1, if a monoalcohol is used, the process produces an ester. As shown in FIG. 2, if a polyol is used, an ester alcohol is made.

The process typically includes the use of an ozonolysis catalyst. The ozonolysis catalyst is generally a Lewis acid or a Bronsted acid. Suitable catalysts include, but are not limited to, boron trifluoride, boron trichloride, boron tribromide, tin halides (such as tin chlorides), aluminum halides (such as aluminum chlorides), zeolites (solid acid), molecular sieves (solid acid), sulfuric acid, phosphoric acid, boric acid, acetic acid, and hydrohalic acids (such as hydrochloric acid). The ozonolysis catalyst can be a resin-bound acid catalyst, such as SiliaBond propylsulfonic acid, or Amberlite® IR-120 (macroreticular or gellular resins or silica covalently bonded to sulfonic acid or carboxylic acid groups). One advantage of a solid acid or resin-bound acid catalyst is that it can be removed from the reaction mixture by simple filtration.

The process generally takes place at a temperature in a range of about −80° C. to about 80° C., typically about 0° C. to about 40° C., or about 10° C. to about 20° C.

The process can take place in the presence of a solvent, if desired. Suitable solvents include, but are not limited to, ester solvents, ketone solvents, chlorinated solvents, amide solvents, or combinations thereof. Examples of suitable solvents include, but are not limited to, ethyl acetate, acetone, methyl ethyl ketone, chloroform, methylene chloride, and N-methylpyrrolidinone.

When the alcohol is a polyol, an ester alcohol is produced. Suitable polyols include, but are not limited to, glycerin, trimethylolpropane, pentaerythritol, or propylene glycol, alditols such as sorbitol and other aldoses and ketoses such as glucose and fructose.

When the alcohol is a monoalcohol, the process may proceed too slowly to be practical in a commercial process and the extended reaction time can lead to undesired oxidation of the monoalcohol by ozone. Therefore, it may be desirable to include an oxidant. Suitable oxidants include, but are not limited to, hydrogen peroxide, Oxone® (potassium peroxymonosulfate), Caro's acid, or combinations thereof.

The use of a modified oil, which has been transesterified to esters at the fatty acid glyceride sites before reacting with the ozone and excess alcohol, allows the production of hybrid $C_9$ or azelate esters (the major component in the reaction mixture) in which the ester on one end of the azelate diester is different from the ester on the other end. In order to produce a hybrid ester composition, the alcohol used in ozonolysis is different from the alcohol used to transesterify the esters at the fatty acid glyceride sites.

The esters produced by the process can optionally be amidified to form amides. One method of amidifying the esters to form amides is by reacting an amine alcohol with the esters to form the amides. The amidifying process can include heating the ester/amine alcohol mixture, distilling the ester/amine alcohol mixture, and/or refluxing the ester/amine alcohol mixture, in order too drive the reaction to completion. An amidifying catalyst can be used, although this is not necessary if the amine alcohol is ethanolamine, due to its relatively short reaction times, or if the reaction is allowed to proceed for suitable periods of time. Suitable catalysts include, but are not limited to, boron trifluoride, sodium methoxide, sodium iodide, sodium cyanide, or combinations thereof.

Figure 7:
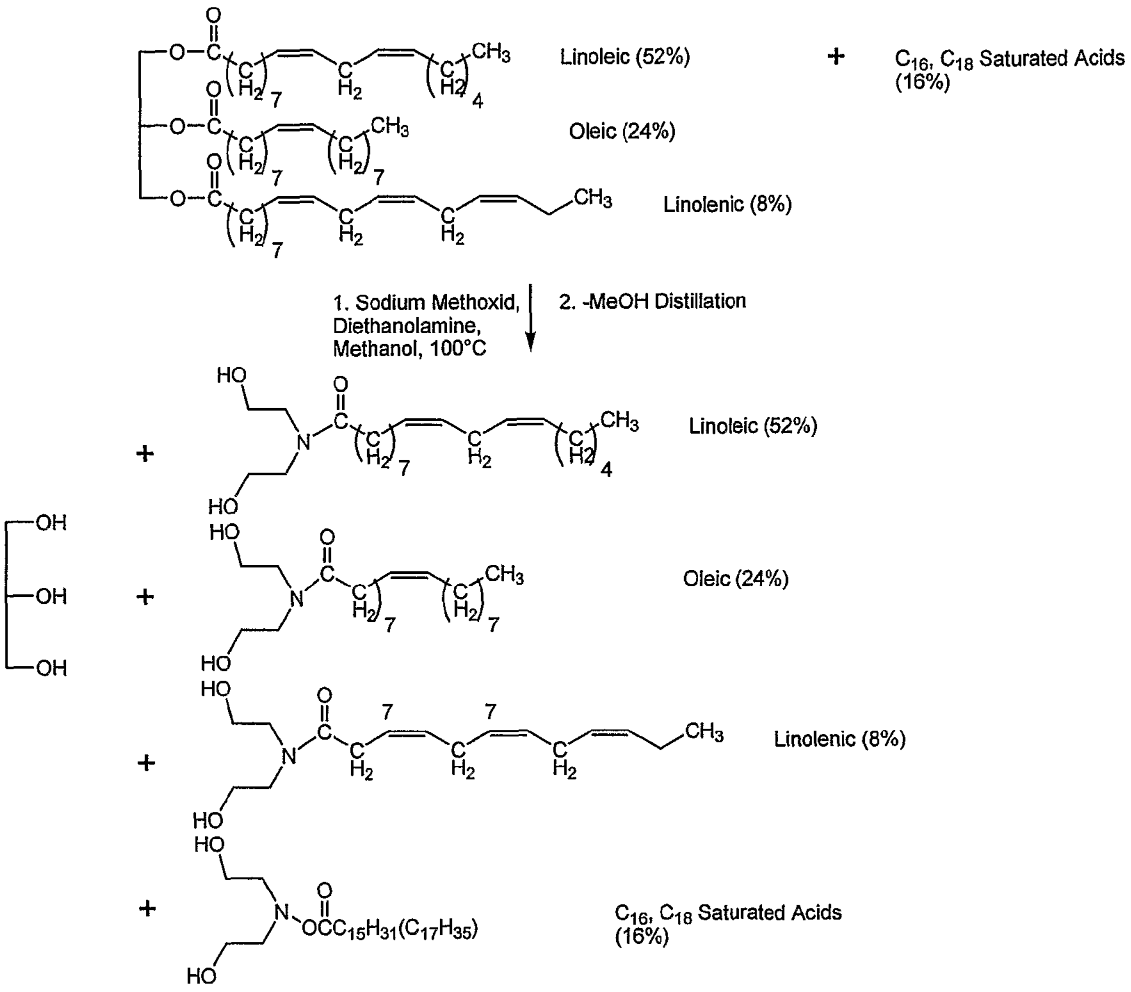
FIG. 7 is a schematic depicting the amidification of triglyceride fatty acids at the triglyceride backbone to generate fatty acid amide alcohols.

Another broad embodiment of the invention provides a method for producing amides. The method includes amidifying a biobased oil, or oil derivative so that substantially all of the fatty acids are amidified at the triglyceride sites, as shown in FIG. 7. The amidified biobased oil, or oil derivative is then reacted with ozone and excess alcohol to produce esters at the double bond sites. This process allows the production of hybrid ester/amides.

The ester in the hybrid ester/amide can optionally be amidified. If a different amine alcohol is used for the initial amidification process from that used in the second amidification process, then $C_9$ or azelaic acid hybrid diamides (the major component in the reaction mixture) will be produced in which the amide functionality on one end of the molecule is different from the amide functionality on the other end.

Ester Polyols

Figure 3:
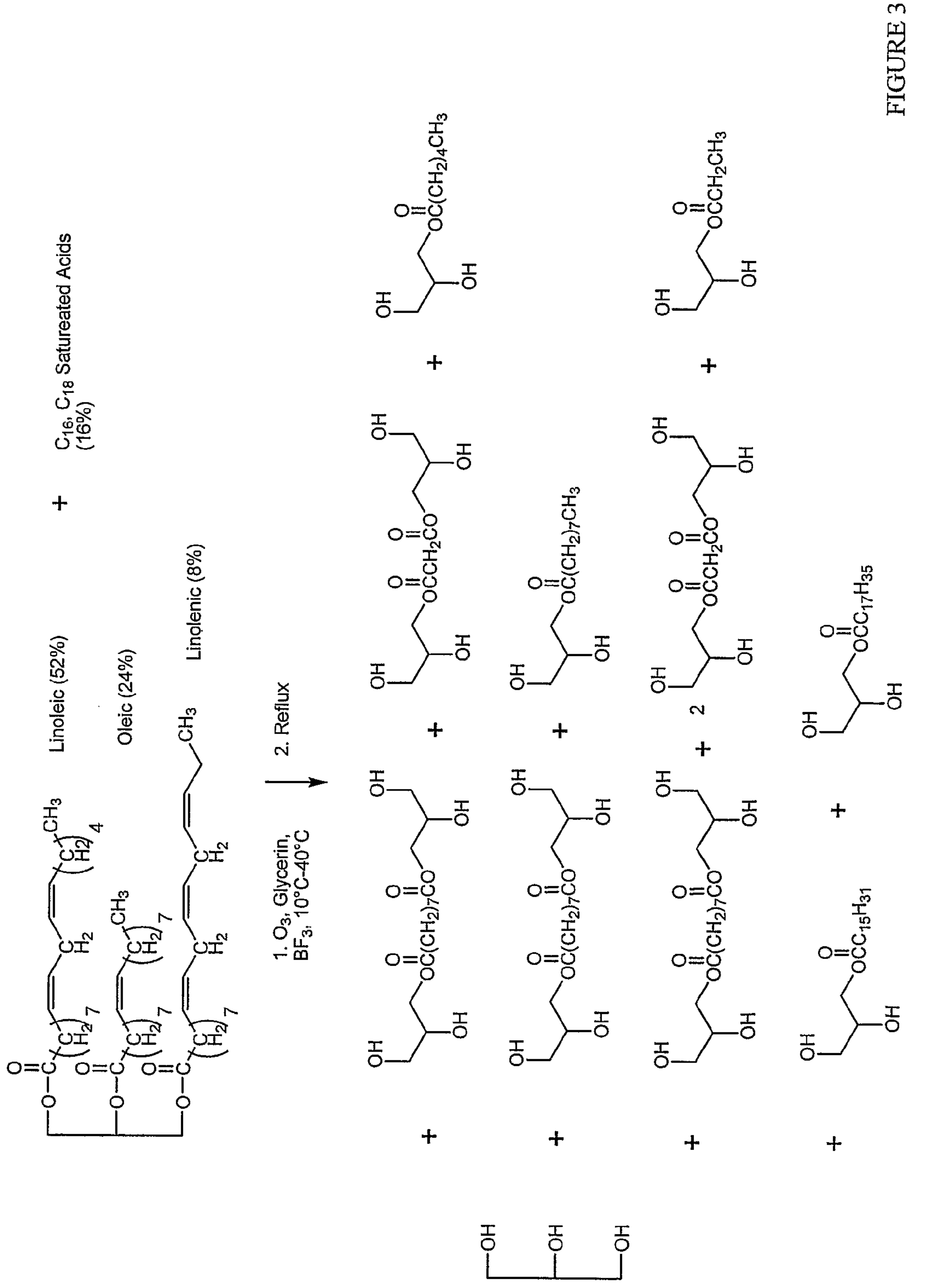
FIG. 3 is a schematic depicting the steps and specific products involved in converting an idealized soybean oil molecule by ozonolysis and triglyceride transesterification in the presence of glycerin and boron trifluoride to an ester alcohol with the relative proportions of the individual fatty acids indicated. The primary processes and products from each fatty acid are shown.

The following section discusses the production of highly functionalized glyceride alcohols (or glyceride polyols) from soybean oil by ozonolysis in the presence of glycerin and boron trifluoride as shown in FIG. 3. Glycerin is a leading ester polyol precursor candidate since it is projected to be produced in high volume as a byproduct in the production of methyl soyate (biodiesel). Other candidate reactant polyols include propylene glycol (a diol), trimethylolpropane (a triol) and pentaerythritol (a tetraol), alditols such as sorbitol and other aldoses and ketoses such as glucose and fructose.

Broadly, ozonolysis of soybean oil is typically performed in the presence of a catalyst, such as catalytic quantities of boron trifluoride (e.g., 0.06-0.25 equivalents), and excess glycerin (e.g. four equivalents of glycerin) (compared to the number of reactive double bond plus triglyceride sites) at about −80° C. to about 80° C. (preferably about 0° C. to about 40° C.) in a solvent such as those disclosed herein.

It is expected that dehydrating agents such as molecular sieves and magnesium sulfate will stabilize the ester product by reducing product ester hydrolysis during the reflux stage based on chemical precedents.

Completion of ozonolysis was indicated by an external potassium iodide/starch test solution, and the reaction mixture was refluxed typically one hour or more in the same reaction vessel. Boron trifluoride was removed by treatment with sodium carbonate, and the resulting ethyl acetate solution was washed with water to remove excess glycerin.

One benefit of using boron trifluoride as the catalyst is that it also functions as an effective transesterification catalyst so that the excess glycerin also undergoes transesterification reactions at the site of original fatty acid triglyceride backbone while partially or completely displacing the original glycerin from the fatty acid. Although not wishing to be bound by theory, it is believed that this transesterification process occurs during the reflux stage following the lower temperature ozonolysis. Other Lewis and Bronsted acids can also function as transesterification catalysts (see the list elsewhere herein).

Combined proton NMR and IR spectroscopy confirmed that the primary processes and products starting with an idealized soybean oil molecule showing the relative proportions of individual fatty acids are mainly 1-monoglycerides as indicated in FIG. 3. However, some 2-monoglycerides and diglycerides are also produced. FIG. 3 illustrates typical reactions for an idealized soybean oil molecule. FIG. 3 also shows that monoglyceride groups become attached to each original olefinic carbon atom and the original fatty acid carboxylic groups are also transesterified primarily to monoglyceride groups to generate a mixture of primarily 1-monoglycerides, 2-monoglycerides and diglycerides. Thus, not only are the unsaturated fatty acid groups multiply derivatized by glycerin, but the 16% saturated fatty acids are also converted primarily to monoglycerides by transesterification at their carboxylic acid sites.

Excess glycerin (four equivalents) was used in order to produce primarily monoglycerides at the double bond sites and minimize formation of diglycerides and triglycerides by further reaction of pendant product alcohol groups with the ozonolysis intermediates. However, diglycerides can still function as polyols since they have available hydroxyl groups. One typical structure for diglycerides is shown below as Formula I.

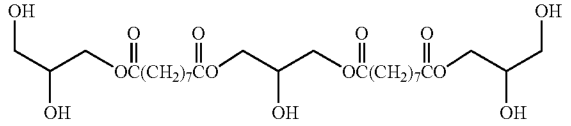

This follows since the higher the concentration of glycerin, the greater the probability that, once a hydroxyl group of a glycerin molecule (preferentially primary hydroxyl groups) reacts with either the aldehyde or carbonyl oxide intermediates, the remaining hydroxyl groups in that molecule will not also be involved in these type reactions.

1-Monoglycerides have a 1:1 combination of primary and secondary hydroxyl groups for preparation of polyarethanes and polyesters. The combination of more reactive primary hydroxyl groups and less reactive secondary hydroxyl groups may lead to rapid initial cures and fast initial viscosity building followed by a slower final cure. However, when using starting polyols comprised substantially exclusively of primary hydroxyl groups such as trimethylolpropane or pentaerythritol, substantially all pendant hydroxyl groups will necessarily be primary in nature and have about equal initial reactivity.

The theoretical weight for the preparation of soybean oil monoglycerides shown above is about two times the starting weight of soybean oil, and the observed yields were close to this factor. Thus, the materials cost for this transformation is close to the average of the per pound cost of soybean oil and glycerin.

Glyceride alcohols obtained were clear and colorless and had low to moderately low viscosities. When ethyl acetate is used as the solvent, hydroxyl values range from 230 to approximately 350, acid values ranged from about 2 to about 12, and glycerin contents were reduced to <1% with two water washes.

When ester solvents such as ethyl acetate are used, there is a potential for a side reaction in the production of vegetable oil glyceride alcohols (example for soybean oil shown in FIG. 3), or ester alcohols in general, that involves the transesterification of the free hydroxyl groups in these products with the solvent ester to form ester-capped hydroxyl groups. When ethyl acetate is used, acetate esters are formed at the hydroxyl sites, resulting in capping of some hydroxyl groups so that they are no longer available for further reaction to produce foams and coatings. If the amount of ester capping is increased, the hydroxyl value will be decreased, thus providing a means to reduce and adjust hydroxyl values. Ester capping may also be desirable since during purification of polyol products by water washing, the water solubility of the product ester alcohol is correspondingly decreased leading to lower polyol product loss in the aqueous layer.

Several methods are available to control ester capping reactions, and thus the hydroxyl value of the ester alcohol.

Figure 6:
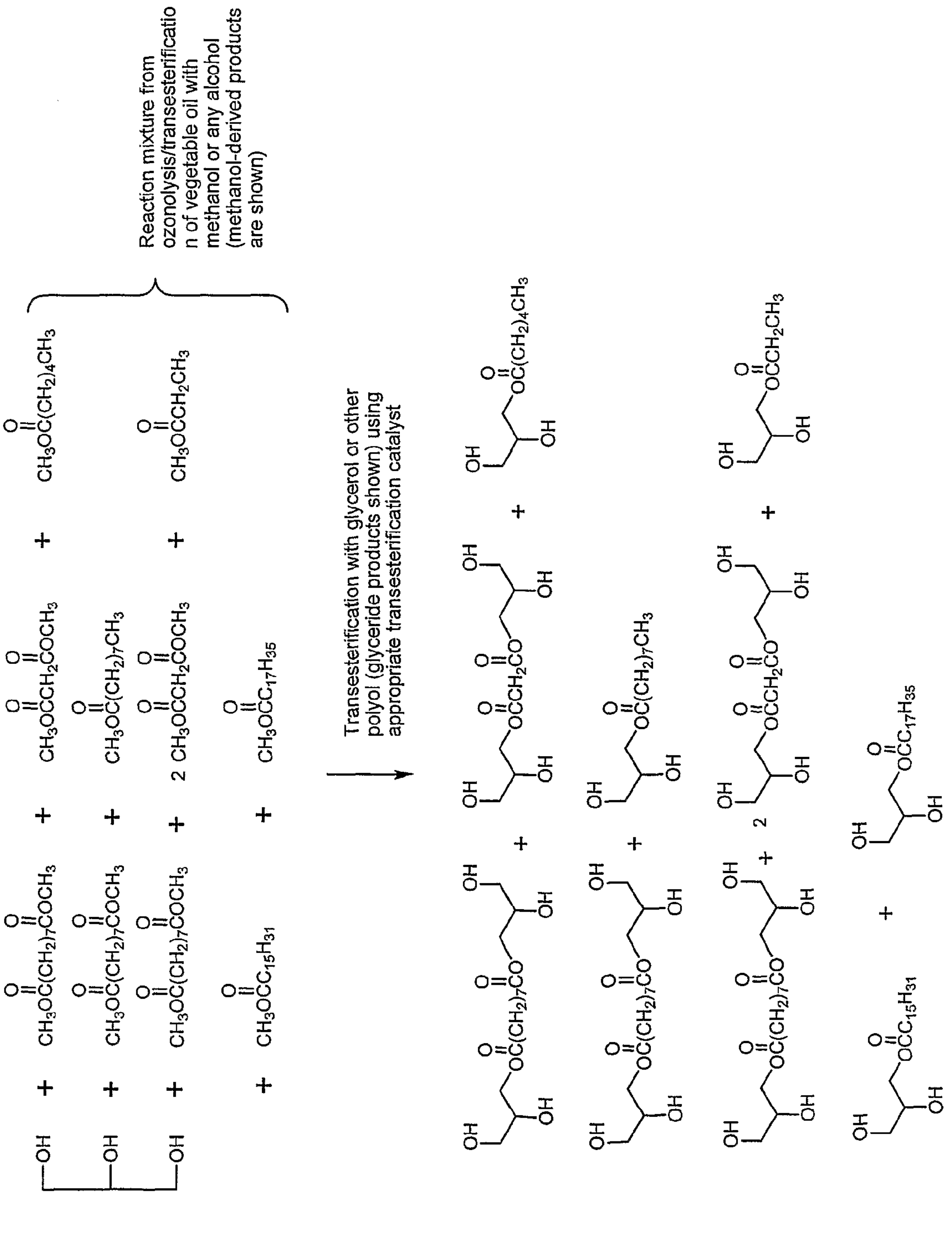
FIG. 6 is a schematic flow diagram showing a method to prepare vegetable oil ester alcohols by initial preparation of alkyl esters followed by transesterification with glycerin or any polyol.

One method is shown in FIG. 6, which illustrates an alternate approach to prepare vegetable oil glyceride alcohols, or ester alcohols in general, by reacting (transesterifying) the vegetable oil methyl ester mixture (shown in FIG. 4), or any vegetable oil alkyl ester mixture, with glycerin, or any other polyol such as trimethylolpropane or pentaerythritol, to form the same product composition shown in FIG. 3, or related ester alcohols if esters are not used as solvents in the transesterification step. Also, if esters are used as solvents in transesterifying the mixture of FIG. 4 (alkyl esters) with a polyol, a shorter reaction time would be expected compared to transesterification of the fatty acids at the triglyceride backbone (as shown in FIG. 3), thus leading to decreased ester capping of the hydroxyl groups. This method has merit in its own right, but involves one extra step than the sequence shown in FIG. 3.

Another method of controlling the ester capping in general is to use solvents that are not esters (such as amides such as NMP (1-methyl-2-pyrrolidinone) and DMF (N,N-dimethyl formamide); ketones, or chlorinated solvents) and can not enter into transesterification reactions with the product or reactant hydroxyl groups. Alternatively, "hindered esters" such as alkyl (methyl, ethyl, etc.) pivalates (alkyl 2,2-dimethylpropionates) and alkyl 2-methylpropionates (isobutyrates) can be used. This type of hindered ester should serve well as an alternate recyclable solvent for vegetable oils and glycerin, while its tendency to enter into transesterification reactions (as ethyl acetate does) should be significantly impeded due to steric hindrance. The use of isobutyrates and pivalates provides the good solubilization properties of esters without ester capping to provide maximum hydroxyl value as desired.

Another way to control the ester capping is to vary the reflux time. Increasing the reflux time increases the amount of ester capping if esters are used as ozonolysis solvents.

Figure 8:
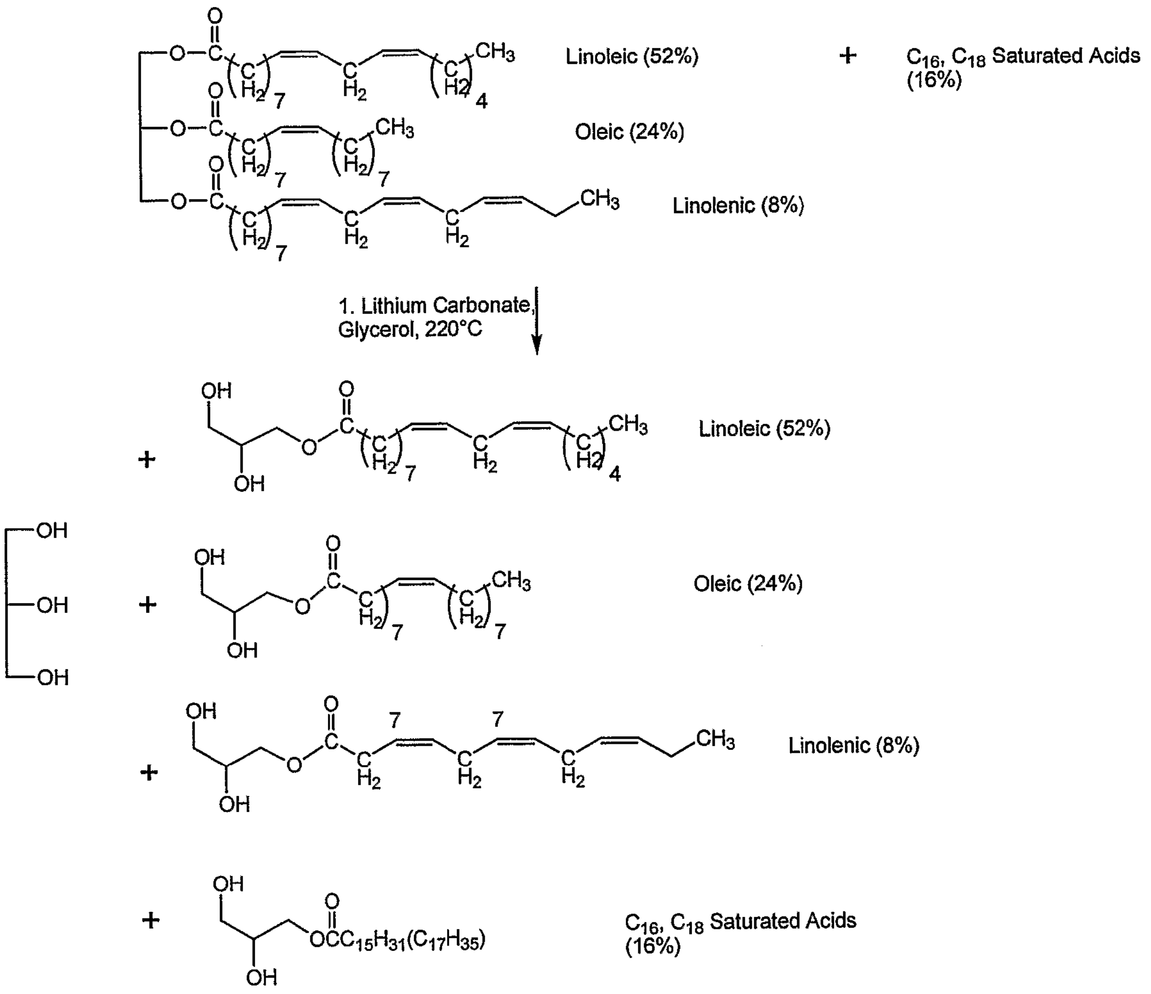
FIG. 8 is a schematic depicting the transesterification of the fatty acids at the triglyceride backbone to generate fatty acid ester alcohols.

Ester capping of polyol functionality can also be controlled by first transesterifying the triglyceride backbone, as shown in FIG. 8 and described in Example 2, and then performing ozonolysis, as described in Example 3, resulting in a shorter reaction time when esters are used as solvents.

Water washing of the product in ethyl acetate solutions has been used to remove the excess glycerin. Because of the high hydroxyl content of many of these products, water partitioning leads to extreme loss of ester polyol yield. It is expected that using water containing the appropriate amount of dissolved salt (sodium chloride or others) will lead to reduced product loss currently observed with water washing. Even though not demonstrated, the excess glycerin used presumably can be separated from water washes by simple distillation.

In order to remove the acid catalyst boron trifluoride effectively without water partitioning, basic resins, such as Amberlyst® A-21 and Amberlyst® A-26 (macroreticular or gellular resins of silica covalently bonded to amine groups or quaternary ammonium hydroxide), have been used. The use of these resins may also be beneficial because of potential catalyst recycling by thermal treatment to release boron trifluoride from either resin or by chemical treatment with hydroxide ion. Sodium carbonate has been used to scavenge and also decompose the boron trifluoride catalyst.

The present invention allows the preparation of a unique mixture of components that are all end functionalized with alcohol or polyol groups. Evidence indicates when these mixtures are reacted with polyisocyanates to form polyurethanes, that the resulting mixtures of polyurethanes components plasticize each other so that a very low glass transition temperature for the mixed polyurethane has been measured. This glass transition is about 100° C. lower than expected based solely on hydroxyl values of other biobased polyols, none of which have been transesterified or amidified at the glyceride backbone. Also, the polyols derived from these cleaved fatty acids have lower viscosities and higher molecular mobilities compared to these non-cleaved biobased polyols, leading to more efficient reactions with polyisocyanates and molecular incorporation into the polymer matrix. This effect is manifested in polyurethanes derived from the polyols of the present invention giving significantly lower extractables in comparison to other biobased polyols when extracted with a polar solvent such as N,N-dimethylacetamide.

Amide Alcohols

Figure 4:
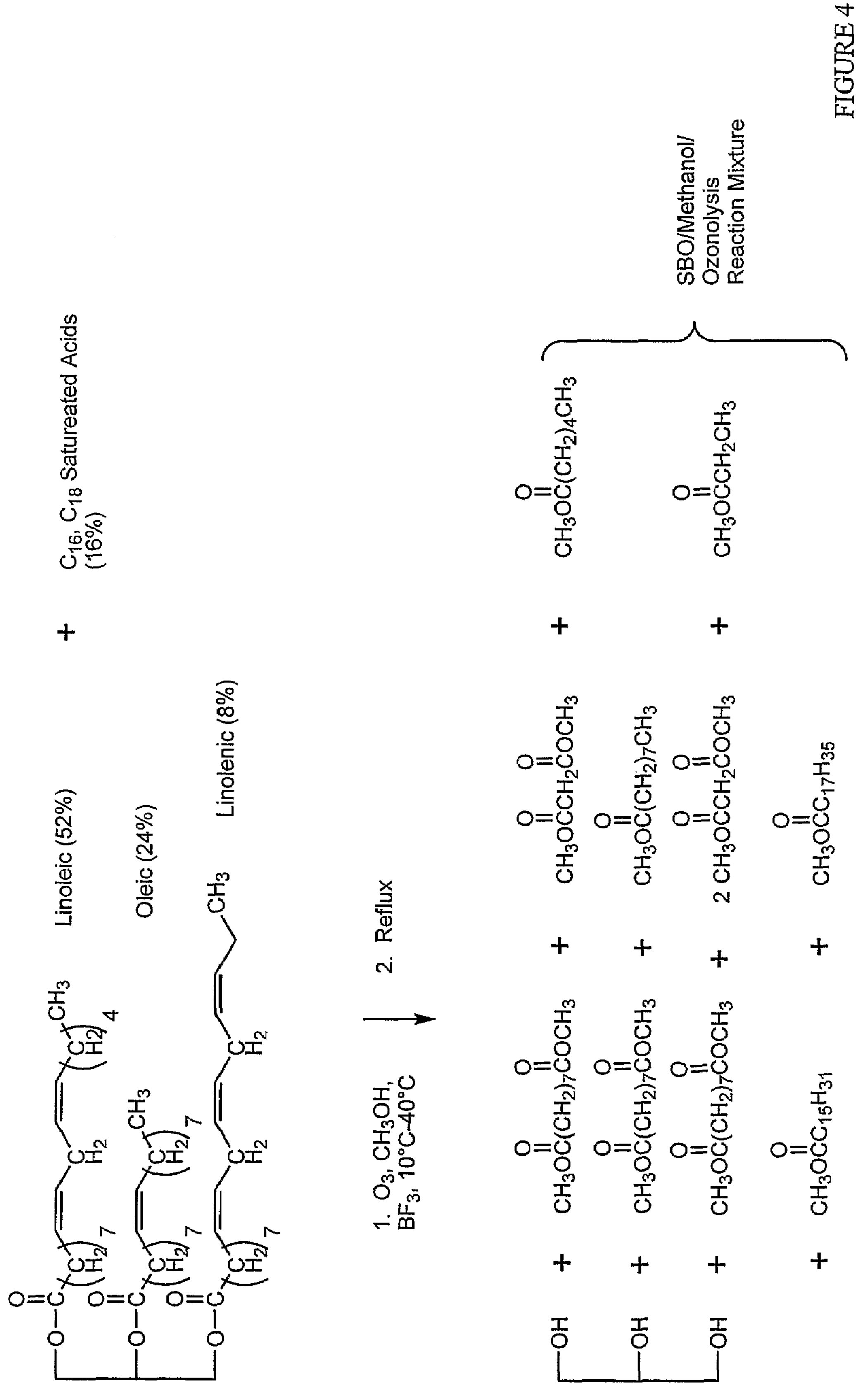
FIG. 4 is a schematic depicting the steps involved in converting an idealized soybean molecule by ozonolysis and triglyceride transesterification in the presence of methanol and boron trifluoride to cleaved methyl esters as intermediates. The primary processes and intermediates from each fatty acid are indicated.
Figure 5:
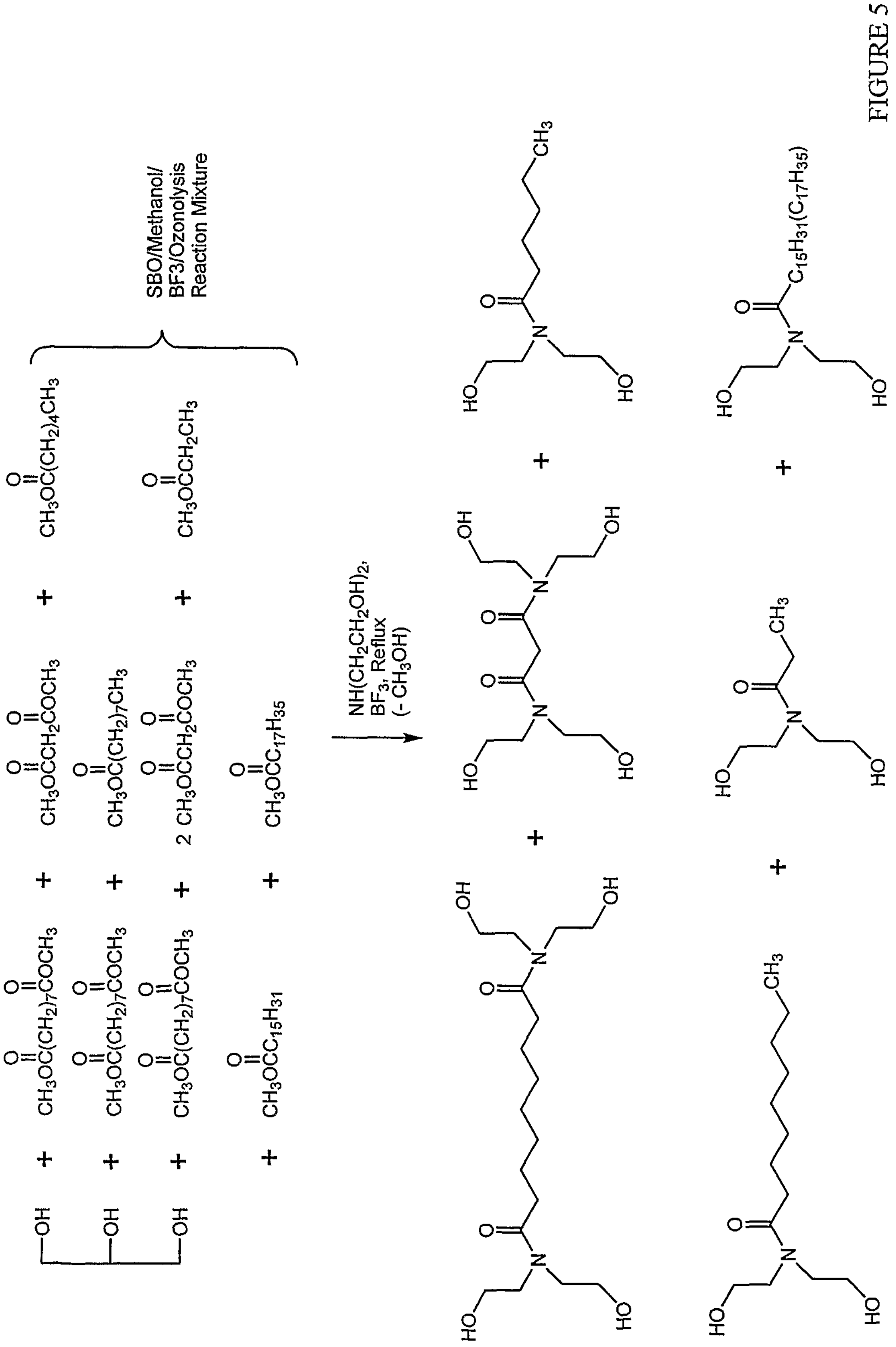
FIG. 5 is a schematic depicting the amidification processes and products starting with the intermediate cleaved methyl esters (after initial ozonolysis and triglyceride transesterification) and then reacting with diethanolamine to produce the final amide alcohol product.

The following section discusses the production of highly functionalized amide alcohols from soybean oil by ozonolysis in the presence of methanol and boron trifluoride followed by amidification with amine alcohols. Refer now to FIGS. 4 and 5.

Ozonolysis of soybean oil was performed in the presence of catalytic quantities of boron trifluoride (0.25 equivalent with respect to all reactive sites) at 20-40° C. in methanol as the reactive solvent. It is anticipated that significantly lower concentrations of boron trifluoride or other Lewis or Bronsted acids could be used in this ozonolysis step (see the list of catalysts specified elsewhere). Completion of ozonolysis was indicated by an external potassium iodide/starch test solution. This reaction mixture was then typically refluxed typically one hour in the same reaction vessel. As stated previously, in addition to serving as a catalyst in the dehydration of intermediate methoxy hydroperoxides and the conversion of aldehydes to acetals, boron trifluoride also serves as an effective transesterification catalyst to generate a mixture of methyl esters at the original fatty acid ester sites at the triglyceride backbone while displacing glycerin from the triglyceride. It is anticipated that other Lewis and Bronsted acids can be used for this purpose. Thus, not only are all double bond carbon atoms of unsaturated fatty acid groups converted to methyl esters by methanol, but the 16% saturated fatty acids are also converted to methyl esters by transesterification at their carboxylic acid sites. Combined proton NMR and IR spectroscopy and GC analyses indicate that the primary processes and products starting with an idealized soybean oil molecule showing the relative proportions of individual fatty acids are mainly as indicated in FIG. 4.

Amidification of the methyl ester mixture was performed with the amine alcohols diethanolamine, diisopropanolamine, N-methylethanolamine, N-ethylethanolamine, and ethanolamine. These reactions typically used 1.2-1.5 equivalents of amine and were driven to near completion by ambient pressure distillation of the excess methanol solvent and the methanol released during amidification, or just heat under reflux, or at lower temperatures. These amidification reactions were catalyzed by boron trifluoride or sodium methoxide which were removed after this reaction was complete by treatment with the strong base resins Amberlyst A-26® or the strong acid resin Amberlite® IR-120, respectively. Removal of boron trifluoride was monitored by flame tests on copper wire wherein boron trifluoride gives a green flame. After amidification reactions with amine alcohols, excess amine alcohols were removed by short path distillation using a Kugelrohr short path distillation apparatus at temperatures typically ranging from 70° C. to 125° C. and pressures ranging from 0.02-0.5 Torr.

Combined proton NMR and IR spectroscopy indicate that the primary amidification processes and products starting with the cleaved methyl esters after initial ozonolysis and then reacting with an amine alcohol such as diethanolamine are mainly as indicated below in FIG. 5. Thus, not only are the unsaturated fatty acid groups of soybean oil multiply converted to amide alcohols or amide polyols at their olefinic sites as well as the fatty acid triglyceride sites, but the 16% saturated fatty acids are also converted to amide alcohols or amide polyols at their fatty acid sites.

The boron trifluoride catalyst may be recycled by co-distillation during distillation of excess diethanolamine, due to strong complexation of boron trifluoride with amines.

One problem that has been identified is the oxidation of monoalcohols such as methanol, that is used both as a solvent and reactant, by ozone to oxidized products (such as formic acid, which is further oxidized to formate esters, when methanol is used). Methods that have been evaluated to minimize this problem are listed below:

(1). Perform ozonolysis at decreased temperatures, ranging from about −78° C. (dry ice temperature) to about 20° C.;

(2). Perform ozonolysis reaction with alcohols less prone to oxidation than methanol such as primary alcohols (ethanol, 1-propanol, 1-butanol, etc.), secondary alcohols (2-propanol, 2-hydroxybutane, etc.), or tertiary alcohols, such as tertiary-butanol;

(3). Perform ozonolysis reaction using alternate ozone non-reactive cosolvents (esters, ketones, tertiary amides, ketones, chlorinated solvents) where any monoalcohol used as a reagent is present in much lower concentrations and thus would compete much less effectively for oxidation with ozone.

The boron trifluoride catalyst may be recycled by co-distillation during distillation of excess diethanolamine, due to strong complexation of boron trifluoride with amines.

All examples herein are merely illustrative of typical aspects of the invention and are not meant to limit the invention in any way.

Example 1

Figure 9:
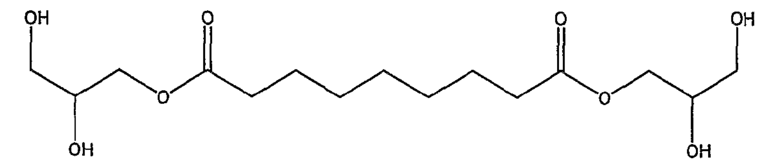
FIG. 9 shows the major azelaic ($C_9$) components in soybean oil ester polyols and mixed polyols.
Figure 9:
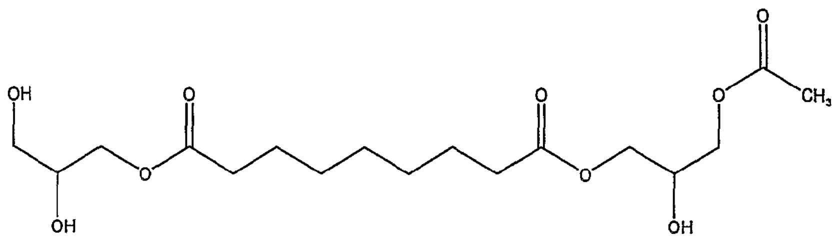
Figure 9:
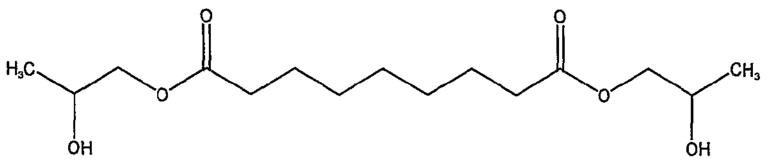
Figure 9:
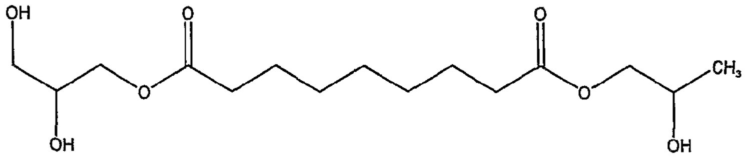

This example shows a procedure for making glyceride alcohols or primarily soybean oil monoglycerides as shown in FIG. 3 (also including products such as those in FIG. 9 A, B, C).

All steps for making glyceride alcohols were performed under a blanket of Argon. The ozonolysis of soybean oil was carried out by first weighing 20.29 grams of soybean oil (0.02306 mole; 0.02036×12=0.2767 mole double bond plus triglyceride reactive sites) and 101.34 grams of glycerol (1.10 mole; 4 fold molar excess) into a 500 mL 3-neck round bottom flask. A magnetic stirrer, ethyl acetate (300 mL) and boron trifluoride diethyl etherate (8.65 mL) were added to the round bottom flask. A thermocouple, sparge tube, and condenser (with a gas inlet attached to a bubbler containing potassium iodide (1 wt %) in starch solution (1%) were attached to the round bottom flask. The round bottom flask was placed into a water-ice bath on a magnetic stir plate to maintain the internal temperature at 10-20° C., and ozone was bubbled through the sparge tube into the mixture for 2 hours until the reaction was indicated to be complete by appearance of a blue color in the iodine-starch solution. The sparge tube and ice-water bath were removed, and a heating mantle was used to reflux this mixture for 1 hour.

After cooling to room temperature, sodium carbonate (33 g) was added to neutralize the boron trifluoride. This mixture was stirred overnight, after which distilled water (150 mL) was added and the mixture was again stirred well. The ethyl acetate layer was removed in a separatory funnel and remixed with distilled water (100 mL) for 3 minutes. The ethyl acetate layer was placed into a 500 mL Erlenmeyer flask and dried with sodium sulfate. Once dry, the solution was filtered using a coarse flitted Buchner funnel, and the solvent was removed in a rotary evaporator (60° C. at approximately 2 Torr). The final weight of this product was 41.20 grams which corresponded to a yield of 84.2% when the theoretical yield was based on the exclusive formation of monoglycerides. The acid and hydroxyl values were 3.8 and 293.1 respectively. Proton NMR Spectroscopy yielded a complex spectrum, but the major portion matched the spectrum of bis(2,3-dihydroxy-1-propyl)azelate based on comparisons to authentic 1-monoglyceride esters.

Example 2

This example shows the production of soybean oil transesterified with propylene glycol or glycerin as shown in FIG. 8.

Soybean oil was added to a flask containing propylene glycol (1 mole soybean oil/6 mole propylene glycol) and lithium carbonate (1.5 wt % of soybean oil), and the flask was heated at 185° C. for 14 hrs. The product was rinsed with hot distilled water and dried. Proton NMR spectroscopy indicated the presence of 1-propylene glycol monoester and no mono-, di- or triglycerides.

When reacting with glycerol, a working ratio of 1 mole soybean oil/20 mole glycerol was used when the reaction was performed at 220° C. for 100 hrs to maximize the amount of monoglycerides that gave a composition containing 70% monoglycerides, 29% diglycerides and a trace of triglyceride (glyceryl soyate).

Example 3

This example shows production of a mixed ester alcohol, as in FIG. 9D.

Soybean oil was initially transesterified with glycerin as specified in Example 2 to produce glyceryl soyate. 50.0 g glyceryl soyate was reacted with ozone in the presence of 130 g propylene glycol, boron trifluoride etherate (13.4 mL) in chloroform (500 mL). The ozonolysis was performed at ambient temperature until indicated to be complete by passing the effluent gases from the reaction into a 1% potassium iodide/starch ozone-indicating solution and refluxing the ozonolysis solution for one hour. The mixture was stirred with 60 g sodium carbonate for 20 hours and filtered. The resulting solution was initially evaporated on a rotary evaporator and a short path distillation apparatus (a Kugelrohr apparatus) was used to vacuum distill the excess propylene glycol at 80° C. and 0.25 Torr. The final product is a hybrid ester alcohol with pendent glycerin and propylene glycol hydroxyl groups with respect to the azelate moiety in the product mixture.

Example 4

This example shows the use of a resin-bound acid to catalyze soybean ozonolysis.

20 g of soybean oil that was pretransesterified with glycerin were reacted with ozone in the presence of 64 g of glycerin, 34 g of SiliaBond propylsulfonic acid (silica bound acid prepared by Silicycle, Inc.), and 300 mL of acetone. Ozone treatment was performed at 15-20° C., followed by a 1 hr reflux. The resin bound acid was filtered and product purified by vacuum distillation. The resulting product composition included about 83% monoglycerides with the balance being diglycerides. The yield was about 88% when the theoretical yield was based on exclusive formation of monoglycerides.

Example 5

Figure 10:
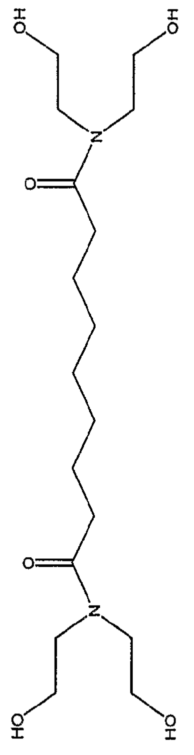
FIG. 10 shows examples of various azelaic amide polyols and hybrid amide polyols which can made using the methods of the present invention.
Figure 10:
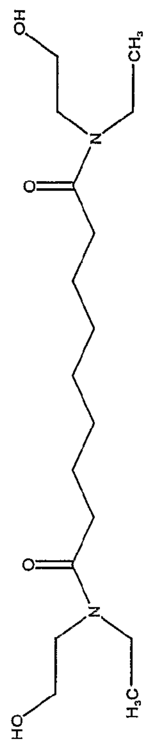
Figure 10:
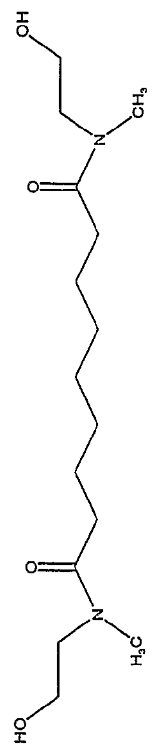
Figure 10:
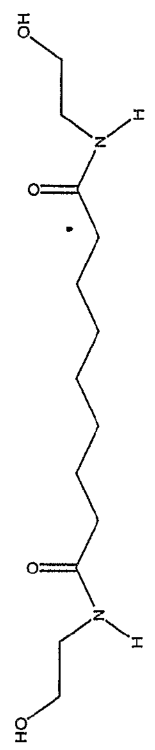
Figure 10:
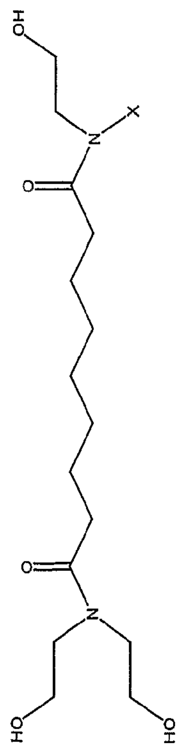

This example shows a procedure for making amide alcohols (amide polyols such as those in FIG. 10 A, B, C, D) starting with methanol-transesterified (modified) soybean oil (a commercial product called Soyclear® or more generally termed methyl soyate).

A problem in making the monoalcohol-derived ester intermediates during ozonolysis of soybean oil with mono-alcohols, such as methanol, in the presence of catalysts such as boron trifluoride is that oxidation of these intermediate acyclic acetals to hydrotrioxides to desired esters is very slow. This has been shown by determining the composition of soybean oil reaction products using various instrumental methods, including gas chromatography. This slow step is also observed when model aldehydes were subjected to ozonolysis conditions in the presence of mono-alcohols and boron trifluoride.

Performing ozonolysis at high temperatures can be used to drive this reaction to completion, but significant problems arise from oxidation of the alcohol and ozone loss due to the long reaction times required. When reactions were performed at low temperatures, the oxidation reaction proceeded slowly and did not progress to completion.

An alternate method for oxidation was developed that effectively used hydrogen peroxide to convert the aldehyde/acetal mixture to the desired carboxylic acid ester. Without wishing to be bound by theory, it is possible that (1) the hydrogen peroxide oxidizes the acetal to an intermediate that rearranges to the ester, or (2) the aldehyde is oxidized to the carboxylic acid by hydrogen peroxide and the carboxylic acid is then esterified to the desired ester.

All steps for making amide alcohols were done under a blanket of Argon.

The first step in preparing amide alcohols was to prepare the methyl esters of methanol transesterified soybean oil. Soyclear® (151.50 grams; 0.1714 mole; 0.1714×9 1.54 mole double bond reactive sites) was weighed into a 1000 mL 3-neck round bottom flask. A magnetic stirrer, methanol (500 mL; 12.34 mole), and 6.52 mL 99% sulfuric acid (0.122 moles) were added to the flask. A thermocouple, sparge tube, and condenser (with a gas inlet attached to a bubbler containing 1 wt % potassium iodide in 1 wt % starch solution) were attached to the round bottom flask. The flask was placed in a water bath on a magnetic stir plate to maintain temperature at 20° C., and ozone was added through the sparge tube into the mixture for 20 hours (at which time close to the theoretical amount of ozone required to cleave all double bonds had been added), after which the iodine-starch solution turned blue. The sparge tube and water bath were removed, a heating mantle was placed under the flask, and the mixture was refluxed for 1 hour. After reflux, 50 percent hydrogen peroxide (95 mL) was added to the mixture and then refluxed for 3 hrs (mixture was refluxed 1 hour longer but to no change was noted). The mixture was then partitioned with methylene chloride and water. The methylene chloride layer was also washed with 10% sodium bicarbonate and 10% sodium sulfite (to reduce unreacted hydrogen peroxide) until the mixture was both neutral and gave no response with peroxide indicating strips. The solution was then dried with magnesium sulfate and filtered. The product was purified by short path distillation to obtain 140.3 g of clear and colorless liquid. This yield could have been improved by initial distillation of the excess methanol or by continued extraction of all aqueous layers with methylene chloride.

The second step involved in preparing amide alcohols involved the reaction of the methyl esters of methanol transesterified soybean oil prepared above with 2-(ethylamino) ethanol (N-ethylethanolamine). 2-(Ethylamino) ethanol (137.01 g; 1.54 mole) was added to a round bottom containing the methyl esters of methanol transesterified soybean oil (135.20 g; 0.116 mole or 1.395 mole total reaction sites), sodium methoxide (15.38 g; 0.285 mole), and methyl alcohol (50 ml). A short path distillation apparatus was attached and the mixture was heated to 100° C. for removal of methanol. The reaction was monitored by the decrease of the IR ester peak at approximately 1735 $cm^{-}1$ and was complete after 3 hours.

After cooling to room temperature, the oil was dissolved in methanol and stirred with 500 mL of Amberlite® IR-120 for 1 hour to neutralize the sodium methoxide. The solutions was filtered and then stirred with 100 mL Amberlyst A-26® resin (hydroxide form). The mixture was filtered, and the resin was washed thoroughly with methanol. The bulk solvent was then removed in vacuo on a rotary evaporator, and the resulting oil was placed on a Kugelrohr system to remove residual excess 2-(ethylamino) ethanol and solvent at a temperature of 30° C. and pressure of 0.04 to 0.2 Torr.

The final weight of the product was 181.85 grams, giving a yield of about 85%. The hydroxyl value was 351.5. The IR peak at 1620 $cm^{-1}$ is indicative of an amide structure. Proton NMR Spectroscopy shows no evidence of triglyceride. NMR peaks at 3.3-3.6 ppm region are indicative of beta-hydroxymethyl amide functionality and are characteristic of amide hindered rotation consistent with these amide structures.

Amide alcohol or amide polyol products obtained from this general process were clear and orange colored and had moderate viscosities. Analogous reactions were performed with the amine alcohol used was diethanolamine, diisopropanolamine, N-methylethanolamine, and ethanolamine.

Example 6

This example shows a low temperature procedure for making the methyl esters of methanol transesterified soybean oil.

Soyclear® (10.0 g; 0.01 mole; 0.10 mole double bond reactive sites) was weighed into a 500 mL 3 neck round bottom flask. A magnetic stirrer, methanol (150 mL), methylene chloride (150 mL), and boron trifluoride diethyl etherate (3.25 mL; 0.03 mole) were added to the flask. A thermometer, sparge tube, and condenser (with a gas inlet attached to a bubbler containing 1 wt % potassium iodide in 1 wt % starch solution) were attached to the round bottom flask. The flask was placed into a dry ice acetone bath on a magnetic stir plate to maintain temperature at −68° C. Ozone was added through a sparge tube into the mixture for 1 hour in which the solution had turned blue in color. The sparge tube and bath was then removed, and the solution allowed to warm to room temperature. Once at room temperature, a sample was taken showing that all double bonds had been consumed. At this point, 50 percent hydrogen peroxide (10 mL) was added to solution, a heating mantle was placed under the flask, and the mixture was refluxed for 2 hours. Sampling revealed the desired products. The mixture was then treated by methylene chloride-water partitioning in which the methylene chloride was washed with 10% sodium bicarbonate and 10% sodium sulfite (to reduce unreacted hydrogen peroxide) until the mixture was both neutral and gave no response with peroxide indicating strips. The solution was then dried with magnesium sulfate and filtered. The product was purified by short path distillation giving moderate yields.

Example 7

This example shows a procedure for making the methyl esters of methanol transesterified soybean oil (shown in FIG. 4).

Soybean oil (128.0 g; 0.15 mole; 1.74 mole double bond reactive sites plus triglyceride reactive sites) was weighed into a 500 mL 3 neck round bottom flask. A magnetic stirrer, methanol (266 mL), and 99 percent sulfuric acid (3.0 mL; 0.06 mole) were added to the flask. A thermocouple and condenser were attached to the round bottom flask. A heating mantle and stir plate was placed under the flask and the mixture was refluxed for 3 hours (in which the heterogeneous mixture becomes homogeneous. The heating mantle was then replaced with a water bath to maintain temperature around 20° C. A sparge tube was attached to the flask and a gas inlet with a bubbler containing 1 wt % potassium iodide in 1 wt % starch solution was attached to the condenser. Ozone was added through a sparge tube into the mixture for 14 hours. The water bath was then replaced with a heating mantle, and the temperature was raised to 45° C. Ozone was stopped after 7 hours, and the solution was refluxed for 5 hours. Ozone was then restarted and sparged into the mixture for 13 hours longer at 45° C. The mixture was then refluxed 2 hours longer. Sampling showed 99.3% complete reaction. The mixture was then treated by methylene chloride-water partitioning in which the methylene chloride was washed with 10% sodium bicarbonate and 5% sodium sulfite (to reduce unreacted hydrogen peroxide) until the mixture was both neutral and gave no response with peroxide indicating strips. The solution was then dried with magnesium sulfate and filtered. The product was purified by short path distillation to obtain 146.3 g of clear and light yellow liquid. Initial distillation of the methanol or continued extraction of all aqueous layers with methylene chloride could have improved this yield.

Example 8

This example illustrates amidification fatty acid-cleaved methyl esters without the use of catalyst.

The methyl esters of methanol transesterified soybean oil (20.0 g; the product of ozonolysis of methyl soyate in methanol described in the first step of Example 5) were added to 25.64 g (2 equivalents) of ethanolamine and 5 mL methanol. The mixture was heated to 120° C. in a flask attached to a short path distillation apparatus overnight at ambient pressure. Thus, the reaction time was somewhat less than 16 hrs. The reaction was shown to be complete by loss of the ester peak at 1730 $cm^{-1}$ in its infrared spectra. Excess ethanolamine was removed by vacuum distillation.

Example 9

This example shows the amidification of fatty acids at the triglyceride backbone sites as shown in FIG. 7.

Backbone amidification of esters can be performed not only using Lewis acids and Bronsted acids, but also using bases such as sodium methoxide.

100.0 g of soybean oil was reacted with 286.0 g of diethanolamine (2 equivalents) dissolved in 200 ml methanol, using 10.50 g of sodium methoxide as a catalyst. The reaction was complete after heating the reaction mixture at 100° C. for three hours during which methanol was collected by short path distillation. The reaction mixture was purified by ethyl acetate/water partitioning to produce the desired product in about 98% yield. Proton NMR spectroscopy indicated a purity of about 98% purity with the balance being methyl esters.

This reaction can also be performed neat, but the use of methanol enhances solubility and reduces reaction times.

The reaction can be performed catalyst free, but slower, with a wide range of amines. See Example 8.

Example 10

Figure 11:
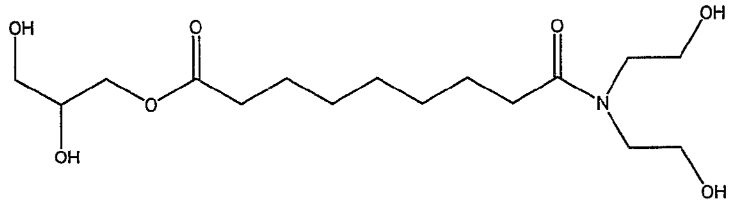
FIG. 11 shows examples of various hybrid soybean ester and amide polyols which can be made using the methods of the present invention.
Figure 11:
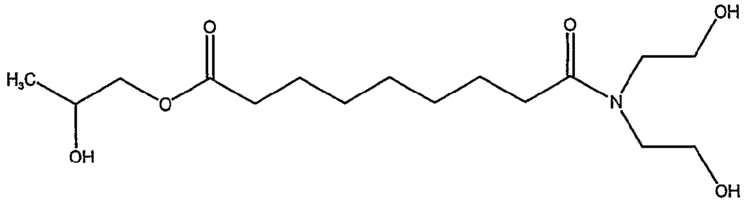
Figure 11:
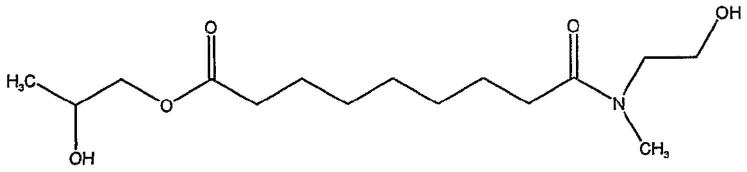

This example shows the use of fatty acids amidified at the triglyceride backbone (soy amides) to produce hybrid soy amide/ester materials such as those shown in FIG. 11.

Soy amides (fatty acids amidified at the triglyceride backbone as described in Example 9) can be converted to an array of amide/ester hybrids with respect in the azelate component. Soybean oil diethanolamide (200.0 g; from Example 9) was ozonized for 26 hours at 15-25° C. in the presence of 500 g of propylene glycol using 1 liter of chloroform as solvent and 51.65 mL of boron trifluoride diethyl etherate. After ozone treatment, the solution was refluxed for 1.5 hours. The reaction mixture was neutralized by stirring the mixture for 3 hours with 166.5 g of sodium carbonate in 300 mL water. These solutions were placed into a 6 liter separatory funnel containing 1350 mL water. The chloroform layer was removed and the water layer was re-extracted with 1325 mL of ethyl acetate. The ethyl acetate and chloroform layers were combined, dried with magnesium sulfate, and then filtered. Solvent was removed on a rotary evaporator and the placed on a Kugelrohr short path distillation apparatus for 2.5 hours at 30° C. at 0.17 Torr. This process yielded 289.25 g of material which constitutes a 81% yield. The hydroxyl value obtained on the material was 343.6.

To illustrate the chemical structure of this mixture, only the resulting azelate component (the major component) would have diethanolamide functionality on one end and the ester of propylene glycol on the other end. (This product could then be further amidified with a different amide to create a hybrid amide system such as the one in FIG. 10 E).

Example 11

This example shows the amidification of soybean oil derivatives to increase hydroxyl value.

Amidification can be applied to oil derivatives, such as hydroformylated soybean oil and hydrogenated epoxidized soybean oil, to increase the hydroxyl value and reactivity.

Hydrogenated epoxidized soybean oil (257.0 g) was amidified with 131 g of diethanolamine with 6.55 g of sodium methoxide and 280 mL methanol using the amidification and purification process described for the amidification of esters in Example 9. The product was purified by ethyl acetate/water partitioning. When diethanolamine was used, the yield was 91% and the product had a theoretical hydroxyl value of 498.

This product has both primary hydroxyl groups (from the diethanolamide structure) and secondary hydroxyl groups along the fatty acid chain.

Example 12

This example shows the transesterification of soybean oil mono-alcohol esters (ethyl and methyl esters) with glycerin to form primarily soybean oil monoglycerides (illustrated in FIG. 6).

8 g of soy ethyl esters (product of ozonolysis and reflux of soybean oil in ethanol with individual structures analogous to those shown in FIG. 4) were added to 30.0 g of glycerin, ethanol (30 mL), and 99% sulfuric acid (0.34 mL). The mixture was heated to 120° C. in a short path distillation apparatus for 6.5 hours. The reaction was analyzed using NMR spectroscopy which showed about 54% glyceride product and balance being ethyl ester starting material. Boron trifluoride diethyl etherate (0.1 mL) was added, and the solution was heated to 120° C. for 5 hours. The reaction was analyzed by NMR spectroscopy which indicated the presence of about 72% total glyceride product with the balance being the ethyl ester starting material.

In another experiment, 30.0 g soy methyl esters (product of ozonolysis and reflux soybean oil in methanol using sulfuric acid as catalyst as illustrated in FIG. 4) were added to 96.8 g. glycerin, methanol (50 mL), and 7.15 g of sodium methoxide (shown in FIG. 6). The mixture was heated to 100° C. for 15.5 hours in a short path distillation apparatus, and the temperature was raised to 130° C. for 2 hr. with vacuum being applied for the final 2 minutes of heating. The reaction was analyzed by NMR spectroscopy which showed 55% total glyceride product with the balance being methyl ester starting materials.

Coatings

Polyurethane and polyester coatings can be made using the ester alcohols, ester polyols, amide alcohols, and amide polyols of the present invention and reacting them with polyisocyanates, polyacids, or polyesters.

A number of coatings with various polyols using specific di- and triisocyanates, and mixtures thereof were prepared. These coatings have been tested with respect to flexibility (conical mandrel bend), chemical resistance (double MEK rubs), adhesion (cross-hatch adhesion), impact resistance (direct and indirect impact with 80 lb weight), hardness (measured by the pencil hardness scale) and gloss (measured with a specular gloss meter set at 60°). The following structures are just the azealate component of select ester, amide, and ester/ amide hybrid alcohols, with their corresponding hydroxyl functionality, that were prepared and tested.

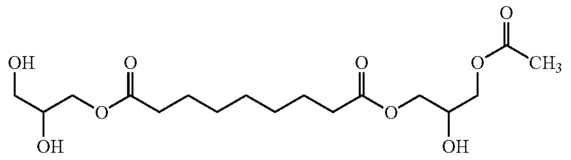
Acetate-Capped Soybean Oil "Monoglycerides"
Hydroxyl Functionality approximately 3

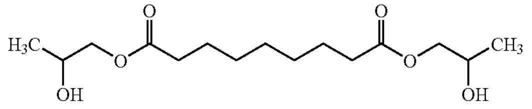
Soybean Oil Propylene Glycol Esters
Hydroxyl Functionality approximately 2

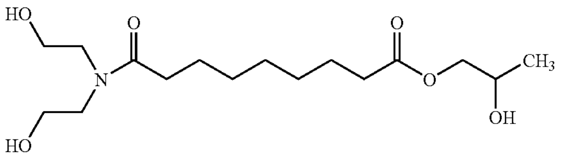
Soybean Oil Mixed Diethanolamide Propylene Glycol Esters
Hydroxyl Functionality approximately 3

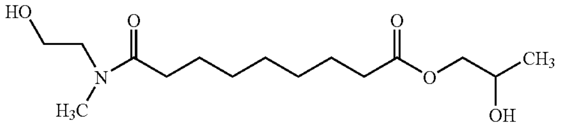
Soybean Oil Mixed N-Methyethanolamine Propylene Glycol Esters
Hydroxyl Functionality approximately 2

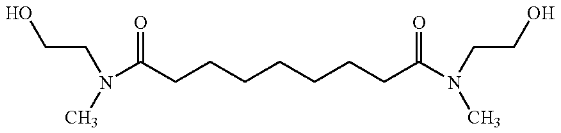
Soybean Oil Mixed N-Methyethanolamine
Hydroxyl Functionality 2

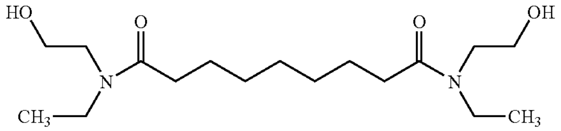
Soybean Oil N-Ethylethanolamide
Hydroxyl Functionality 2

The following commercial isocyanates (with commercial names, abbreviations and isocyanate functionality) were used in the coatings work: diphenylmethane 4,4'-diisocyanate (MDI, difunctional); Isonate 143L (MDI modified with a carbodiimide, trifunctional at <90° C. and difunctional at >90° C.); Isobond 1088 (a polymeric MDI derivative); Bayhydur 302 (Bayh. 302, a trimer of hexamethylene 1,6-diisocyanate, trifunctional); and 2,4-toluenediisocyanate (TDI, difunctional).

Coatings were initially cured at 120° C. for 20 minutes using 0.5% dibutyltin dilaurate, but it became evident that curing at 163° C. for 20 minutes gave higher performance coatings so curing at the higher temperature was adopted. A minimum pencil hardness needed for general-use coatings is HB and a hardness of 2H is sufficiently hard to be used in many applications where high hardness is required. High gloss is valued in coatings and 60° gloss readings of 90-1000 are considered to be "very good" and 60° gloss readings approaching 1000 match those required for "Class A" finishes.

Example 13

Coatings from Partially Acetate-Capped (and Non-Capped) Soybean Oil Monoglycerides Polyurethane coatings were prepared from three different partially acetate-capped samples having different hydroxyl values as specified in Table 1 and numerous combinations of isocyanates were examined.

When using polyol batch 51056-66-28, most coatings were prepared from mixtures of Bayhydur 302 and MDI and it was determined that quite good coatings were obtained when underindexing with these isocyanate mixtures compositions (0.68-0.75 indexing). Two of the best coatings were obtained at a 90:10 ratio of Bayhydur 302:MDI where pencil hardness values of F and H were obtained (formulas 12-2105-4 and 12-2105-3). A very good coating was also obtained when 51056-66-28 was reacted with a 50:50 ratio of Bayhydur 302:MDI. The fact that these good coatings could be obtained when isocyanate was under indexed by about 25% could result from the fact that when the approximately trifunctional polyol reacts with isocyanates with >2 functionality, a sufficiently crosslinked structure is established to provide good coating properties while leaving some of the polyol functionality unreacted.

Polyol batch 51056-6-26, which has a somewhat lower hydroxyl value than 51056-66-28, was mainly reacted with mixtures of Bayhydur 302, Isobond 1088, and Isonate 143L with isocyanate indexing of 0.9-1.0. As can be seen, some very good coatings were obtained, with formulas 2-0206-3 and 2-2606-1 (10:90 ratio of Bayhydur 302:Isobond 1088) being two of the best coatings obtained.

A sample of polyol 51056-6-26 was formulated with a 2:1 mixture of TDI and Bayhydur 302 with no solvent and the viscosity was such that this mixture was applied well to surfaces with an ordinary siphon air gun without requiring any organic solvent. This coating cured well while passing all performance tests and had a 60° gloss of 97°. Such polyol/isocyanate formulations not containing any VOCs could be important because formulation of such mixtures for spray coatings without using organic solvents is of high value but difficult to achieve.

Polyol batch 51056-51-19 had an appreciably lower hydroxyl value than those of polyol batches 51056-66-28 or 51056-6-26 due to a different work-up procedure. This polyol was reacted mainly with mixtures of Bayhydur 302 and MDI. Formulas 2-2606-7 (90:10 Bayhydur 302:MDI and indexed at 1.0) gave an inferior coating in terms of hardness compared to that of polyol 51056-66-28 when reacted with the same, but underindexed, isocyanate composition (formula 12-2105-4).

One coating was obtained using non-capped soybean oil monoglycerides (51290-11-32) that had a hydroxyl value of approximately 585. This coating was prepared by reaction with a 50:50 ratio of Bayhydur 302:MDI (formula 3-0106-1) using approximately 1.0 indexing and had a 2H pencil hardness and a 60° gloss of 99°. This coating was rated as one of the best overall coatings prepared.

Example 14

Coatings from Soybean Oil Propylene Glycol Esters

Preparation and performance data of soybean oil propylene glycol esters are shown in Table 2. Significantly fewer isocyanate compositions were evaluated compared to the soybean oil monoglycerides described in Table 1. The isocyanate compositions that were evaluated with these propylene glycol esters did not correspond to the best compositions evaluated with the glycerides since the favorable data in Table 1 was obtained after the tests with soybean oil propylene glycol esters were initiated.

Coating formula 1-2306-5 was one of the best performing propylene glycol ester/isocyanate compositions that employed a 90:10 ratio of Isobond 1088:Bayhydur 302, with an isocyanate indexing of 1.39. The one test area requiring improvement was that its pencil hardness was only HB. This isocyanate composition is the same as the two high-performing glyceride coatings, formulas 2-2606-1 and 2-2606-3 but these had isocyanate indexing values of 1.0 and 0.90, respectively. The fact that these glyceride-containing coatings had better performance properties is probably due to this indexing difference. Coating formula 1-2306-4 was another relatively high performing coating derived from propylene glycol that was also derived from Isobond 1088 and Bayhydur 302 (with an isocyanate indexing of 1.39) but its pencil hardness was also HB.

Example 15

Soybean Oil-Derived Coatings Containing Hydroxyethylamide Components

Preparation and performance data of this class of polyurethane derivatives is shown in Table 3.

Soybean Oil Diethanolamide (Backbone)-Propylene Glycol Esters

100% Bayhydur 302 gave a better coating in terms of hardness with polyol 51056-95-28 when the isocyanate indexing was 1.00 compared to 0.44 (formulas 2-2606-3 compared to 1-2606-1). Using 100% Isonate 143L and Isobond 1088 with isocyanate indexing of 1.00 gave inferior coatings compared to use of Bayhydur 302.

A polyurethane composition was also prepared with polyol 51056-95-28 using a 2:1 composition of 2,4-TDI:Bayhydur 302 and 10% of a highly branched polyester was added as a "hardening" agent. This coating passed all performance tests and had a pencil hardness of 5H and a 60° gloss of 115°. These results strongly indicate that use of very small quantities of such hardening agents will significantly enhance the performance of polyurethane coatings not only prepared from these hydroxyethylamide-containing coatings but also the glyceride-based and propylene glycol-based coatings as well.

Soybean Oil N-Methylethanolamide (Backbone)-Propylene Glycol Esters

The use of 50:50 Bayhydur 302:MDI with isocyanate indexing of only 0.57 gave good coating results with an exceptional 60° gloss of 101° but the coating pencil hardness was only HB.

Soybean Oil Fully Amidified with N-Methylethanolamine

The use of 100% Isonate 143L with an isocyanate indexing of 0.73 gave a coating that tested well except it had poor chemical resistance (based on MEK rubs) and only had a pencil hardness of HB.

TABLE 1

Test Results of Polyurethane Coatings [a] Prepared from Acetate-Capped Soybean Oil "Monoglyceride"

| | NCO/OH Ratio// | | | | | Coatings Test Results | | | | | | | |
|---|---|---|---|---|---|---|---|---|---|---|---|---|---|
| | Cure | Isocyanate Percentage | | | | Conical | MEK | Cross- | Direct | Reverse | Pencil | | 60 |
| Sample LRB [b]/ Formula Code | Temp. (° C.) | MDI | Isonate 143L | Isobond 1088 | Bayh. 302 | Mandrel Bend | Rubs (100) | hatch Adhesion | Impact (80 lb) | Impact (80 lb) | Hard-ness [c] | After-tack, Thumbprint | Degree Gloss |
| 51056-66-28/ 12-2105-10 | .75// 120 | | | | 100 | P | P (SI dull) | P | P | P | 5B | — | — |
| 51056-66-28/ 12-2105-2 | .75// 163 | | | | 100 | P | P (Dulled) | P | P | P | 4B | — | — |
| 51056-66-28/ 12-2105-12 | .75// 120 | 10 | | | 90 | P | P | P | P | P | HB | — | 94.1 |
| 51056-66-28/ 12-2105-3 | .68// 163 | 10 | | | 90 | P | P | P | P | P | F | — | 101.0 |
| 51056-66-28/ 12-2105-4 ** | .75// 163 | 10 | | | 90 | P | P | P | P | P | H | — | 89.0 |
| 51056-66-28/ 12-2105-14 | .75// 120 | 30 | | | 70 | P | P (SI dull) | P | P | P | 5B | — | — |
| 51056-66-28/ 12-2105-6 | .75// 163 | 30 | | | 70 | P | P | P | P | P | HB | — | — |
| 51056-66-28/ 12-2105-16 | .75// 120 | 50 | | | 50 | P | F | P | P | P | 5B | — | — |
| 51056-66-28/ 12-2105-7 | .68// 163 | 50 | | | 50 | P | P | P | P | P | HB | — | — |
| 51056-66-28/ 12-2105-8 | .75// 163 | 50 | | | 50 | P | P | P | P | P | F | — | 90.2 |
| 51290-11-32 [d]/ 3-0106-1 ** | 1.00// 163 | 50 | | | 50 | P | P | P | P | P | 2H | None | 98.9 |
| 51056-51-19/ 1-1906-2 | 1.22// 163 | | | | 100 | P | P | P | P | P | HB | Very slight | — |
| 51056-51-19/ 2-2606-2 | 1.0// 163° C. | | | | 100 | P | P | P | P | P | 4B | Very slight | 82.6 |
| 51056-51-19/ 2-2606-7 | 1.0// 163° C. | 10 | | | 90 | P | P | P | P | P | 4B | None | 76 |
| 51059-51-19/ 2-2706-3 | 0.90// 163° C. | 10 | | | 90 | P | P | P | P | P | HB | Very slight | 79.9 |
| 51056-51-19/ 2-2606-8 | 1.0// 163° C. | | 100 | | | P | F @ 5 | F (80%) | P | P | HB | None | 97.7 |

TABLE 1-continued

Test Results of Polyurethane Coatings [a] Prepared from Acetate-Capped Soybean Oil "Monoglyceride"

| Sample LRB [b]/ Formula Code | NCO/OH Ratio// Cure Temp. (° C.) | Isocyanate Percentage MDI | Isonate 143L | Isobond 1088 | Bayh. 302 | Coatings Test Results: Conical Mandrel Bend | MEK Rubs (100) | Cross-hatch Adhesion | Direct Impact (80 lb) | Reverse Impact (80 lb) | Pencil Hardness [c] | After-tack, Thumbprint | 60 Degree Gloss |
|---|---|---|---|---|---|---|---|---|---|---|---|---|---|
| 51056-51-19/ 2-2606-9 | 1.0// 163° C. | 100 | | | | F | F @ 10 | F (40%) | F P (40) | P | 4B | None | 98.7 |
| 51290-6-26/ 2-0206-1 | .90// 163° C. | | | | 100 | P | P | P | P | P | 4B | Slight | — |
| 51290-6-26/ 2-0206-2 | .90// 163° C. | | | 50 | 50 | P | P | P | P | P | HB | None | 94.0 |
| 51290-6-26/ 2-0206-3 ** | .90// 163° C. | | | 90 | 10 | P | P | P | P | P | H | None | 96.2 |
| 51290-6-26/ 2-2606-1 ** | 1.0// 163° C. | | | 90 | 10 | P | P | P | P | P | 2H | None | 96.6 |
| 51290-6-26/ 2-0206-4 | .90// 163° C. | | 50 | | 50 | P | P | P | P | P | HB | None | 97.0 |
| 51290-6-26/ 2-0206-5 | .90// 163° C. | | 90 | | 10 | P | F @ 6 | P | P | P | HB | None | — |

[a] Coating are 1.5-2.0 mils mm thick (dry) and cured with 0.5% (of total composition) dibutyltin dilaurate for 20 minutes.

[b] Hydroxyl Values: 51056-65-28 (288), 51056-51-19 (215), 51920-6-26 (250).

[c] Pencil Hardness scale: (softest) 5B, 4B, 3B, 2B, B, HB, F, H, 2H through 9H (hardest).

[d] 51290-11-32: Uncapped monoglyceride having Hydroxyl Vaule of approximately 585.

** Four of the best overall coatings prepared in Phase 2 work.

TABLE 2

Test Results of Polyurethane Coatings [a] Prepared from Soybean Oil "All Propylene Glycol" Esters

| Sample LRB/ Formula Code | NCO/OH Ratio// Cure Temp. (° C.) | Isocyanate Percentage MDI | Isonate 143L | Isobond 1088 | Bayh. 302I | Coatings Test Results: Conical Mandrel Bend | MEK Rubs (100) | Cross-hatch Adhesion | Direct Impact (80 lb) | Reverse Impact (80 lb) | Pencil Hardness | After-tack, Thumbprint | 60 Degree Gloss |
|---|---|---|---|---|---|---|---|---|---|---|---|---|---|
| 51920-9-25/ 2-2706-7 | 1.00// 163 | | | 100 | | P | F @ 5 | P | P | P | B | None | 86.0 |
| 52190-9-25/ 1-2306-4 | 1.39// 163 | | | 50 | 50 | P | P (SI dull) | P | P | P | HB | None | 95.6 |
| 52190-9-25/ 1-2306-5 | 1.39// 163 | | | 90 | 10 | P | P (SI dull) | P | P | P | HB | None | — |
| 52190-9-25/ 1-2506-1 | 1.39// 163 | | 100 | | | P | F @ 7 | F 40% | F | F | 5B | None | — |
| 51920-9-25/ 2-2606-6 | 1.00// 163 | | 100 | | | P | F @ 5 | P | P | P | 5B | Very slight | 98.4 |
| 52190-9-25/ 1-2506-2 | 1.39// 163 | | 50 | 50 | | F | F @ 7 | F 60% | F | F | 5B | None | — |
| 51920-9-25/ 2-2606-11 | 1.00// 163 | | | | 100 | Film was too sticky to run tests | | | | | | | |
| 51920-9-25/ 2-2606-12 | 1.00// 163 | 100 | | | | P | F @ 5 | P | P | P | 5B | Very slight | 96.2 |

[a] Coating are 1.5-2.0 mils mm thick (dry) and cured with 0.5% (of total composition) dibutyltin dilaurate for 20 minutes.
[b] Hydroxyl Value of 52190-9-25: 201
[c] Pencil Hardness scale: (softest) 5B, 4B, 3B, 2B, B, HB, F, H, 2H through 9H (hardest).

Test Results of Polyurethane Coatings [a] Prepared from Soybean Oil Hydroxyethylamide Derivatives

| Sample LRB/ Formula Code | NCO/OH Ratio// Cure Temp. (° C.) | Isocyanate Percentage MDI | Isonate 143L | Isobond 1088 | Bayh. 302 | Coatings Test Results: Conical Mandrel Bend | MEK Rubs (100) | Cross-hatch Adhesion | Direct Impact (80 lb) | Reverse Impact (80 lb) | Pencil Hard-ness | After-tack, Thumbprint | 60 Degree Gloss |
|---|---|---|---|---|---|---|---|---|---|---|---|---|---|
| Soybean Oil Diethanolamide (Backbone)-Propylene Glycol Esters | | | | | | | | | | | | | |
| 51056-95-28/ 2-2706-5 | 1.00// 163 | | 100 | | | P | F @ 15 | F (40%) | F | P | HB | None | 98 |
| 51056-95-28/ 1-2606-1 | .44// 163 | Compare To 12-2105-17! | | | 100 | P | P | P | P | P | HB | Very slight | |
| 51056-95-28/ 2-2606-3 | 1.00// 163 | | | | 100 | P | P | P | P | P | F | None | 86.3 |
| 51056-95-28/ 2-2606-10 | 1.00// 163 | 100 | | | | F | P | F (60%) | P | P | HB | None | 102.7 |
| 51056-95-28/ 2-2706-6 | 1.00// 163 | | | 100 | | F | F @ 80 | F (65%) | P | P | HB | None | 71.6 |
| 51056-95-28/ 1-2706-2 | .44// 163 | | 50 | 50 | | P | F @ 10 | P (90%) | p | P | HB | None | |
| 51056-95-28/ 1-2706-4 | .44// 163 | | 25 | 25 | 50 | P | F @ 7 | P | P | P | 5B | None | |
| 51056-95-28/ 1-2706-5 | .44// 163 | | 37.5 | 37.5 | 25 | P | F @ 10 | P | P | P | 4B | None | |
| Soybean Oil N-Methylethanolamide (backbone)-Propylene Glycol Esters | | | | | | | | | | | | | |
| 51056-73-31/ 12-1505-5 | .57// 163 | 50 | | | 50 | P | P | P | P | P | HB | None | 101.0 |
| 51056-73-31/ 1-0506-2 | .63// 163 | | 100 | | | P | F @ 5 | P | P | P | 5B | None | |
| 51056-73-31/ 1-0506-4 | .63// 163 | 10 | 90 | | | P | F @ 5 | P | P | P | 5B | None | |
| SBO Methyl Esters Fully Amidified with N-Methylethanolamine | | | | | | | | | | | | | |
| 51056-79-33/ 1-1006-1 | .73// 163 | | 100 | | | P | F @ 5 | P | P | P | HB | None | |
| 51056-79-33/ 1-1006-2 | .73/ 163 | 10 | 90 | | | P | F @ 5 | P | P | P | HB | None | |

[a] Coating are 1.5-2.0 mils mm thick (dry) and cured with 0.5% (of total composition) dibutyltin dilaurate for 20 minutes.
[b] Hydroxyl Values: 51056-95-28 (343), 51056-73-31 (313), 51056-79-33 (291).
[c] Pencil Hardness scale: (softest) 5B, 4B, 3B, 2B, B, HB, F, H, 2H through 9H (hardest).

Polyurethane foams can be made using the ester alcohols, ester polyols, amide alcohols, and amide polyols of the present invention and reacting them with polyisocyanates. The preparation methods of the present invention allow a range of hydroxyl functionalities that will allow the products to fit various applications. For example, higher functionality gives more rigid foams (more crosslinking), and lower functionality gives more flexible foams (less crosslinking).

While the forms of the invention herein disclosed constitute presently preferred embodiments, many others are possible. It is not intended herein to mention all of the possible equivalent forms or ramifications of the invention. It is to be understood that the terms used herein are merely descriptive, rather than limiting, and that various changes may be made without departing from the spirit of the scope of the invention.

The invention claimed is:

1. A method for producing an ester comprising:

A. reacting a biobased oil, oil derivative, or modified oil with ozone and excess alcohol in the presence of a solvent at a temperature between about −80° C. to about 80° C. to produce intermediate products; and B. refluxing the intermediate products or reacting the intermediate products at lower than reflux temperature, wherein esters are produced from the intermediate products at double bond sites; and substantially all of the fatty acids are transesterified to esters at the fatty acid glyceride sites.

2. The method of claim 1 wherein the biobased oil, oil derivative, or modified oil is reacted in the presence of an ozonolysis catalyst.

3. The method of claim 1 further comprising reacting a hydroxyl group on the ester with an ester solvent to reduce a hydroxyl value of the ester alcohol.

4. The method of claim 1 wherein the alcohol is a polyol, and wherein the ester is an ester alcohol.

5. The method of claim 1 wherein the alcohol is a monoalcohol.

6. The method of claim 1 wherein the modified oil is an oil which has been transesterified to esters at the fatty acid glyceride sites before reacting with the ozone and excess alcohol.

7. The method of claim 6 wherein the excess alcohol used in ozonolysis is different from an alcohol used to transesterify the esters at the glyceride sites, and wherein a hybrid diester is produced.

8. A method for producing amides comprising:

A. reacting a biobased oil, oil derivative, or modified oil with ozone and excess alcohol in the presence of a solvent at a temperature between about −80° C. to about 80° C. to produce intermediate products;

B. refluxing the intermediate products or reacting the intermediate products at lower than reflux temperature, wherein esters are produced from the intermediate products at double bond sites; and substantially all of the fatty acids are transesterified to esters at the fatty acid glyceride sites; and C. amidifying the esters to form amides.

9. The method of claim 8 wherein amidifying the esters to form amides comprises reacting an amine alcohol with the esters to form the amide alcohol.

10. The method of claim 8 wherein amidifying the esters to form amides takes place in the presence of an amidifying catalyst.

11. The method of claim 2 wherein the ozonolysis catalyst is selected from Lewis acids and Bronsted acids.

12. The method of claim 2 wherein the ozonolysis catalyst is selected from boron trifluoride, boron trichloride, boron tribromide, tin halides, aluminum halides, zeolites, molecular sieves, sulfuric acid, phosphoric acid, boric acid, acetic acid, and hydrohalic acids, or combinations thereof.

13. The method of claim 2 wherein the ozonolysis catalyst is a resin-bound acid.

14. The method of claim 1 wherein the biobased oil, oil derivative, or modified oil is reacted at a temperature in the range of about 0° C. to about 40° C.

15. The method of claim 1 wherein the solvent is selected from ester solvents, ketone solvents, chlorinated solvents, amide solvents, or combinations thereof.

16. The method of claim 4 wherein the polyol is selected from glycerin, trimethylolpropane, pentaerythritol, 1,2-propylene glycol, 1,3-propylene glycol, ethylene glycol, sorbitol, glucitol fructose, glucose, sucrose, aldoses, ketoses, alditols, or combinations thereof.

17. The method of claim 5 further comprising adding an oxidant at step B.

18. The method of claim 17 wherein the oxidant is selected from hydrogen peroxide, potassium peroxymonosulfate, Caro's acid, ozone or combinations thereof.

19. The method of claim 9 wherein amidifying the esters to form amides includes a process selected from heating the ester/amine alcohol mixture, distilling the ester/amine alcohol mixture, refluxing the ester/amine alcohol mixture.

20. The method of claim 10 wherein the amidifying catalyst is selected from boron trifluoride, sodium methoxide, sodium iodide, sodium cyanide, or combinations thereof.

21. The method of claim 9 wherein the amine alcohol is selected from ethanolamine, diethanolamine, N-methylethanolamine, N-ethylethanolamine and tris(hydroxylmethyl) aminomethane.

* * * * *